United States Patent
Hoffman (12)

(10) Patent No.: US 6,280,190 B1
(45) Date of Patent: *Aug. 28, 2001

(54) DENTAL SALIVA EJECTOR TUBE ASSEMBLY

(76) Inventor: Elliott S. Hoffman, 5001 Desert Jewel Dr., Paradise Valley, AZ (US) 85253

( * ) Notice: Subject to any disclaimer, the term of this patent is extended or adjusted under 35 U.S.C. 154(b) by 0 days.

This patent is subject to a terminal disclaimer.

(21) Appl. No.: 09/366,235

(22) Filed: Aug. 3, 1999

Related U.S. Application Data

(63) Continuation-in-part of application No. 09/014,838, filed on Jan. 28, 1998, now Pat. No. 5,931,671, and a continuation-in-part of application No. 09/344,027, filed on Jun. 25, 1999.

(51) Int. Cl.$^7$ .................................................. A61C 17/06
(52) U.S. Cl. ............................................................. 433/91
(58) Field of Search ................................. 433/91, 93, 94, 433/95, 96, 126, 127, 129; 604/103, 283; 285/311, 312, 320

(56) References Cited

U.S. PATENT DOCUMENTS

| | | | |
|---|---|---|---|
| 2,873,528 | 2/1959 | Thompson | 433/96 |
| 3,453,735 | 7/1969 | Burt | 433/96 |
| 3,874,712 | 4/1975 | Watson | 285/236 |
| 4,083,115 | 4/1978 | McKelvey | 433/93 |
| 4,204,328 | 5/1980 | Kutner | 433/29 |
| 4,405,163 | 9/1983 | Voges et al. | 285/305 |
| 4,436,125 | 3/1984 | Blenkush | 141/330 |
| 4,822,278 | 4/1989 | Oliva et al. | 433/91 |
| 4,850,984 | 7/1989 | Harris | 604/326 |
| 4,966,551 | 10/1990 | Betush | 433/95 |
| 4,969,879 | 11/1990 | Lichte | 604/283 |
| 5,267,984 | 12/1993 | Doherty | 604/283 |
| 5,651,771 | 7/1997 | Tangherlini et al. | 604/158 |

OTHER PUBLICATIONS

Jan. 1997 Darby Dental Supply Co. Inc. Catalog Excerpt; page 298.

Primary Examiner—John J. Wilson
(74) Attorney, Agent, or Firm—Cahill, Sutton & Thomas P.L.C.

(57) ABSTRACT

A socket for removably receiving a dental saliva ejector tube includes a central body having a first end forming a port for being coupled to a vacuum hose. The central body includes a passage extending therethrough from the first end toward a second opposing end. An elastic sleeve is secured over the second end of the central body for receiving the end of the ejector tube. A pair of spreader members are secured to the elastic sleeve. A pair of levers are pivotally secured about the central body and are actuated by the user to pull the spreader members apart, thereby distending the elastic sleeve to more easily receive the dental saliva ejector tube. To prevent the ejector tube from becoming dislodged during use, a rib may extend about the lower end of the ejector tube. Alternatively, a seal is formed between the ejector tube and the socket via an o-ring located inside the socket; in this embodiment, the elastic sleeve is omitted, and the levers operate latch mechanisms that selectively engage the rib on the ejector tube.

28 Claims, 3 Drawing Sheets

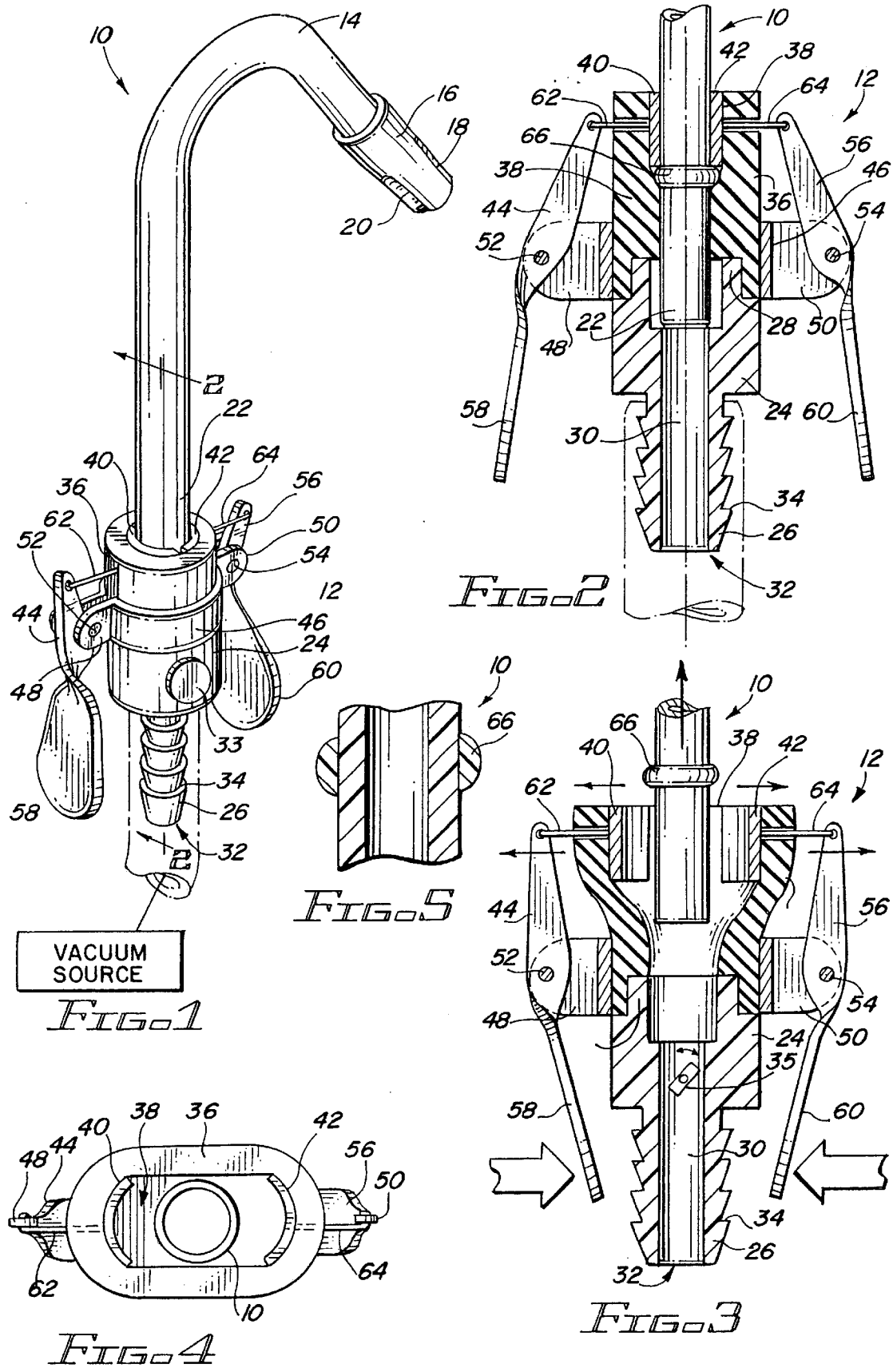

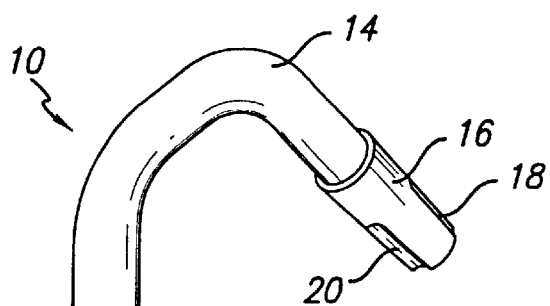
FIG. 6
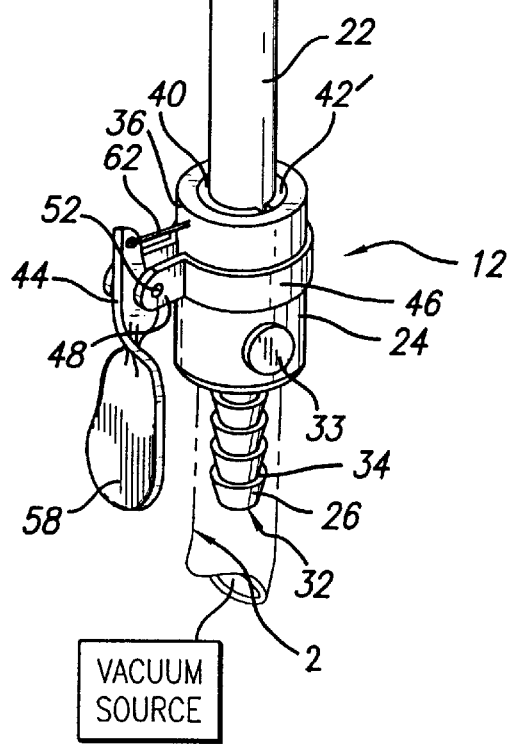
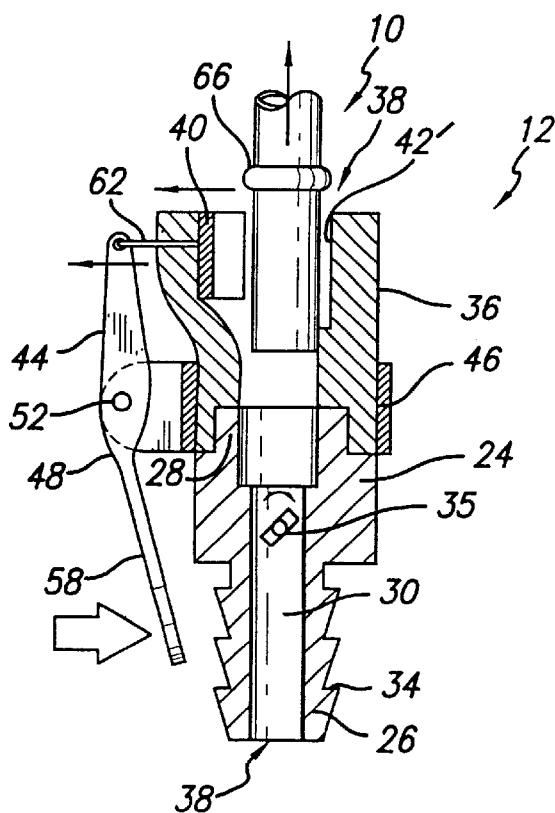
FIG. 7
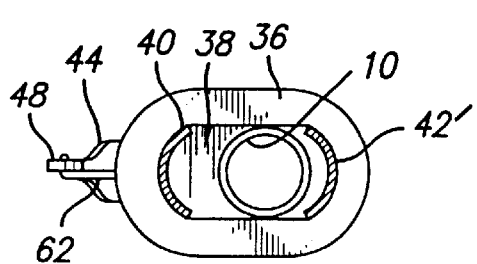
FIG. 8

FIG. 9
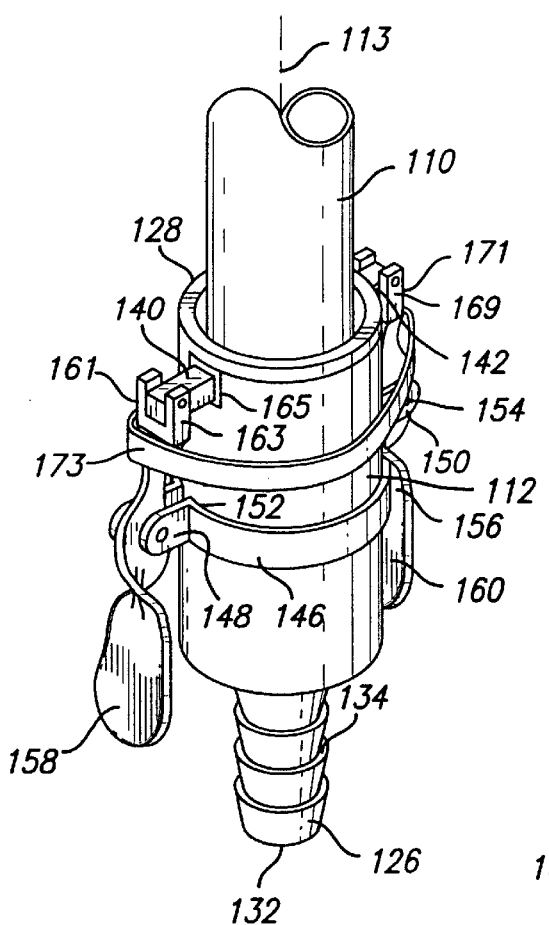
FIG. 10
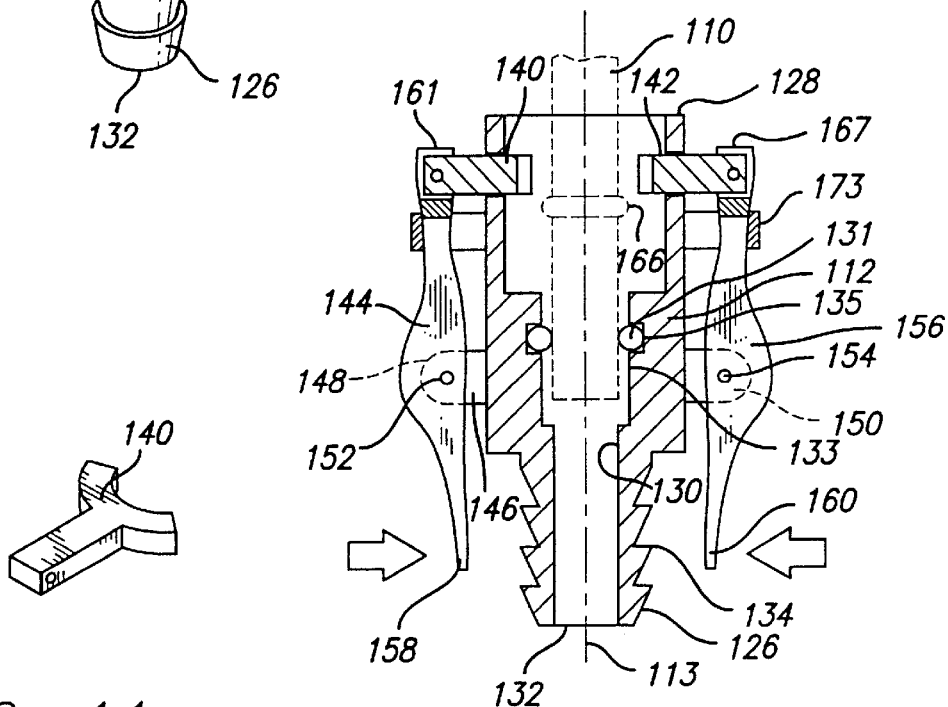
FIG. 11
FIG. 12

DENTAL SALIVA EJECTOR TUBE ASSEMBLY

CROSS-REFERENCE TO RELATED PATENT APPLICATIONS

The present application is a continuation-in-part of parent patent application Ser. No. 09/014,838, filed on Jan. 28, 1998, now U.S. Pat. No. 5,931,671, and a continuation-in-part of patent application Ser. No. 09/344,027, filed on Jun. 25, 1999, and the benefit of the filing dates of such earlier-filed applications under 35 U.S.C. § 120, is hereby claimed.

BACKGROUND OF THE INVENTION

1. Field of the Invention

The present invention relates to dental saliva ejector tubes, and more particularly, to vacuum sockets for releasably receiving dental saliva ejector tubes for applying a source of vacuum thereto.

2. Description of the Relevant Art

In the dental profession, dentists must remove accumulated saliva, water, and other fluids from a patient's mouth, both to keep the work area clear and to avoid the need for the dental patient to swallow such fluids. Typically, the dentist makes use of a dental saliva ejector tube, along with an associated vacuum line, for such purpose. Examples of devices proposed in the past for use by dentists in removing fluids from the patient's mouth are shown in U.S. Pat. No. 2,873,528 to Thompson, U.S. Pat. No. 3,453,735 to Burt, U.S. Pat. No. 4,083,115 to McKelvey, and U.S. Pat. No. 4,204,328 to Kutner.

In one commonly used form of dental saliva ejector tube, one end of the dental saliva ejector tube is bent to form an inverted U-shape and is inserted into the patient's mouth to aspirate collected fluids. The second, or lower end, of the dental saliva ejector tube is typically inserted into a rubber fitting or grommet secured to a vacuum line. The vacuum line may include a valve for selectively closing off the vacuum. Once the dental saliva ejector tube is inserted into the rubber fitting, the dentist may, from time to time, twist or rotate the lower end of the dental saliva ejector tube within such fitting in order to change the angle at which the upper end of the dental saliva ejector tube extends from the rubber fitting. The aforementioned dental saliva ejector tubes are currently commercially available, for example, from Spencer-Meade located in Westbury, N.Y. under the model number 951–9250; these dental saliva ejector tubes are adapted to be inserted into vacuum line sockets that are commercially available by Spencer-Meade located in Westbury, N.Y. under the model number 951–9220.

The aforementioned dental saliva ejector tubes are disposable, and a fresh dental saliva ejector tube is used for each new patient. Because they are disposable, and because a dentist may use many of such dental saliva ejector tubes each day, it is desirable that the dental saliva ejector tube itself be of relatively simple and inexpensive construction. The present inventor has noted that many dentists, dental technicians, and dental assistants experience difficulty inserting the lower end of the dental saliva ejector tube. The rubber fitting or grommet has an opening that is undersized relative to the diameter of the dental saliva ejector tube in order to form a tight seal about the lower end of the dental saliva ejector tube. In addition, the dental saliva ejector tube must be somewhat pliant, rather than rigid, so that the upper half of the tube can be bent into the aforementioned inverted U-shape. The pliancy of the dental saliva ejector tube makes it more difficult to force the lower end of the dental saliva ejector tube into the opening of the rubber fitting.

A further problem experienced by dentists is that such dental saliva ejector tubes sometimes become inadvertently dislodged from the rubber fitting or grommet, as when the vacuum line becomes temporarily snagged on an object and is pulled away from the patient's mouth. In such instances, the dental saliva ejector tube must be reinserted back into the rubber fitting, thereby interrupting the procedure in which the dentist was engaged.

Accordingly, it is an object of the present invention to provide a socket of a vacuum line for removably receiving an end of a dental saliva ejector tube which simplifies the insertion of the dental saliva ejector tube into the socket.

It is another object of the present invention to provide such a vacuum line socket which allows the dental saliva ejector tube to be easily removed therefrom when a dentist has finished working upon a dental patient.

It is still another object of the present invention to provide such a vacuum line socket which allows the dental saliva ejector tube to be rotated following insertion to change the angle at which the bent upper end of the dental saliva ejector tube extends relative to the vacuum line socket.

A further object of the present invention is to provide a dental saliva ejector tube assembly including a dental saliva ejector tube and a vacuum line socket wherein the opening of the vacuum line socket can be selectively modified to facilitate insertion and/or removal of the lower end of the dental saliva ejector tube.

A still further object of the present invention is to provide such a dental saliva ejector tube assembly wherein it is less likely to inadvertently dislodge the dental saliva ejector tube from the vacuum line socket.

Yet another object of the present invention is to provide such a dental saliva ejector tube assembly having the aforementioned advantages while retaining a simple and inexpensive Construction.

These and other objects of the present invention will become more apparent to those of skill in the art as the description of the present invention proceeds.

SUMMARY OF THE INVENTION

Briefly described, and in accordance with the preferred embodiments thereof, the present invention relates to a vacuum line socket and dental saliva ejector tube assembly that includes a dental saliva ejector tube having a first end for being inserted into a patient's mouth and having a second end, said second end having an enlarged diameter retaining rib formed thereupon. The assembly also includes a vacuum line socket having first and second opposing ends and a central passage extending therebetween along a central axis. The first end of the vacuum line socket includes a vacuum port for being coupled to a source of a vacuum; this port is preferably barbed to form a snug fit with a vacuum hose. The second end of the vacuum line socket forms a socket for receiving the second end of the dental saliva ejector tube. Optionally, the vacuum line socket may include a valve for selectively closing the central passage extending therethrough to shut down the vacuum, as when the dental saliva ejector tube is being changed, or is not being used.

At least one lever is pivotally secured to the vacuum line socket, preferably by a supporting bracket extending about the vacuum line socket. The lever includes a lower end adapted to be operated by a user, and an opposing upper end. A latch mechanism is associated with the upper end of the lever and is disposed generally proximate the second end of the vacuum line socket. Operation of the lower end of the lever by the user moves the upper end of the lever and the associated latch mechanism away from the central axis to allow the lower end of the ejector tube to be inserted into, or removed from, the vacuum line socket. The latch mechanism is adapted to engage the enlarged diameter retaining rib formed upon the second end of said dental saliva ejector tube, except in those instances when the user moves the latch mechanism away from the central axis. A biasing member, such as an elastic band, normally biases the upper end of the lever, and its associated latch mechanism, toward the central axis for allowing the latch mechanism to engage the retaining rib of the ejector tube.

If desired, two such opposing levers may be included, each having a latch mechanism of the type described above associated with the upper end thereof. In this event, the upper end of each such lever, as well as the latch mechanism associated therewtih, are normally biased toward the central axis of the vacuum line socket to engage the enlarged diameter retaining rib formed upon the lower end of the dental saliva ejector tube. Operation of the lower ends of the opposing evers by a user causes the upper ends of the levers, and their associated latch mechanisms, to move away from the central axis of the vacuum line socket, apart from each other, away from the second end of the dental saliva ejector tube, and away from the enlarged diameter retaining rib formed thereupon, for allowing the dental saliva ejector tube to be inserted within, or released from, the vacuum line socket.

BRIEF DESCRIPTION OF THE DRAWINGS

FIG. 1 is a perspective view of a dental saliva ejector tube assembly in accordance with the present invention and including a dental saliva ejector tube and a mating vacuum line socket.

FIG. 2 is a cross-sectional drawing of the dental saliva ejector tube assembly shown in FIG 1, in its rest position, i.e., when it is not being actuated by the user's thumb and forefinger.

FIG. 3 is a cross-sectional drawing similar to that of FIG. 2 but showing the levers of the vacuum line socket being depressed by the user's thumb and forefinger to facilitate removal of the dental saliva ejector tube from the vacuum line socket.

FIG. 4 is a top view of the vacuum line socket showing the enlarged opening of the elastic sleeve component of the vacuum line socket when the levers are actuated, as indicated in FIG. 3.

FIG. 5 is an enlarged sectional view of the lower end of the dental saliva ejector tube and illustrating an optional rib extending therefrom.

FIG. 6 is a perspective view of an alternate embodiment of the assembly shown in FIG. 1 but using a single lever.

FIG. 7 is a cross-sectional drawing of the single-lever embodiment shown in FIG. 6 and showing the lever of the vacuum line socket being depressed by the user to facilitate removal of the dental saliva ejector tube from the vacuum line socket.

FIG. 8 is a top view of the vacuum line socket of FIGS. 6 and 7 showing the enlarged opening of the elastic sleeve component of the vacuum line socket when the lever is actuated, as indicated in FIG. 7.

FIG. 9 is a perspective view of another embodiment of the present invention wherein a movable latch mechanism prevents the ejector tube from being inadvertently dislodged from the vacuum line socket.

FIG. 10 is a top view of the assembly shown in FIG. 9.

FIG. 11 is a perspective view of the latch mechanism shown in FIGS. 9 and 10.

FIG. 12 is a cross-sectional view of the assembly shown in FIGS. 9 and 10.

DETAILED DESCRIPTION OF THE PREFERRED EMBODIMENTS

A dental saliva ejector tube assembly constructed in accordance with a first embodiment of the present invention is shown in FIG. 1, wherein reference numeral 10 generally identifies the dental saliva ejector tube and reference numeral 12 generally identifies the vacuum line socket. Ejector tube 10 is made of a pliable plastic for allowing the upper end 14 thereof to be bent into an inverted U-shape for extending over the jaw of a patient. Such ejector tubes may include a thin metal wire (not shown) embedded within the plastic and extending therealong to help keep ejector tube 10 in such bent shape, rather than returning to its original straight configuration. Upper end 14 terminates in a slotted inlet cap 16 adapted to extend within the patient's mouth; slots 18 and 20 communicate with the inner channel of ejector tube 10 and serve to suction saliva, water, and other accumulated fluids out of the patient's mouth. The lower end 22 of ejector tube 10 is circular in shape and is intended to be coupled to a source of a vacuum.

Vacuum line socket 12 is adapted to removably receive lower end 22 of dental saliva ejector tube 10. As shown best in FIGS. 2 and 3, socket 12 includes a central body 24 having a first (or lower) end 26 and a second (or upper) opposing end 28. A central passage 30 extends between first end 26 and opposing second end 28 along a central axis for communicating a vacuum applied at first end 26 to second end 28. First end 26 includes a tapered port 32 for being coupled to a vacuum hose, indicated in dashed outline in FIGS. 1 and 2, which vacuum hose is coupled to a source of a vacuum and waste depository. As indicated in FIGS. 1–3, tapered port 32 may include barbs 34 for retaining tapered port 32 onto the vacuum hose. Central body 24 is preferably made of plastic or hard rubber. An optional control valve 35 (see FIG. 3) may be incorporated within central body 24 to selectively close central passage 30 and block the vacuum source from reaching opening 38; control valve 35 can be rotated manually by control knob 33 (see FIG. 1) to open or close the vacuum. Such a feature can be useful as when closing off the vacuum when the dental saliva ejector tube assembly is not in use.

The second or upper end 28 of central body 24 is in the form of a reduced diameter collar. An elastic sleeve 36, formed of pliable rubber, is secured over and around the reduced diameter collar formed at upper end 28 of central body 24 in a manner described in greater detail below. sleeve 36 has an opening or passage 38 for receiving lower end 22 of dental saliva ejector tube 10. When at rest, in its relaxed state, the inner diameter of sleeve 36 is slightly smaller than the outer diameter of ejector tube 10 to form an airtight seal thereabout.

It will be recalled that one of the objects of the present invention is to facilitate the insertion and removal of lower end 22 of ejector tube 10 into and from socket 12. Toward such purpose, a pair of spreader members 40 and 42 are provided proximate opening 38 of sleeve 36 For enlarging opening 38 when the first and second spreader members 40 and 42 are moved apart from each other. In the preferred embodiment shown in FIGS. 1–4 first and second spreader members 40 and 42 are disposed just inside opening 38 of sleeve 36. Opening 38 is generally circular. Preferably, spreader members 40 and 42 are arcuately shaped, but the arcs thereof are defined by a somewhat larger radius than is true for the outer diameter of ejector rube 10. Accordingly, spreader members 40 and 42 tend to distort the normally circular opening 38 into a more oval shape near the upper end of sleeve 36

As shown in FIGS. 1–3, a metal bracket 46 encircles central body 24 and the lower end of sleeve 36. Bracket 46 serves to clamp the lower end of sleeve 36 about upper end 28 of central body 24. Bracket 46 may be comprised of two metal strips, each including a semicircular middle region terminating in a pair of opposing flanges or ears 48 and 50 that extend in opposing directions away from central body 24. These two metal strips extend about opposing sides of central body 24 and sleeve 36. The two strips of metal forming bracket 46 are secured to each other by hinge pins 52 and 54 which extend through the respective ears 48 and 50, respectively, to the two metal strips.

Socket 12 further includes first and second levers 44 and 56, each of which is pivotally secured by one of hinge pins 52 and 54, respectively. Thus, hinge pins 52 and 54 and bracket 46 pivotally secure each of levers 44 and 56 to central body 24. The lower ends 58 and 60 of levers 44 and 56 are twisted through an angle of ninety degrees relative to the opposing upper ends of levers 44 and 56 to provide a control surface that can be easily depressed by a user's thumb and forefinger during use.

The upper end of first lever 44 is coupled by a thin wire 62 to the first spreader member 40. Likewise, the upper end of second lever 56 is coupled by thin wire 64 to second spreader member 42. Thin wires 62 and 64 extend through small apertures formed in sleeve 36. When levers 44 and 56 are not actuated by a user, the natural elasticity of sleeve 38 pulls spreader 28 members 40 and 42 toward each other (prior to insertion of dental saliva ejector tube 10) or against the outer walls of the dental saliva ejector tube 10 (after insertion of such dental saliva ejector tube) as shown in FIG. 2. The portions of sleeve 36 below spreader members 40 and 42 seal about the outer walls of tube 10 to form an airtight seal thereabout.

At such times that a user desires to either insert a new ejector tube 10, or to remove an existing ejector tube 10, the user grasps the lower ends 58 and 60 of levers 44 and 56 with the users thumb and forefinger, and squeezes them together in the manner indicated in FIGS. 3 and 4. this causes the upper ends of levers 44 and 56 to move apart from each other, thereby pulling spreader members 40 and 42 apart from each other, for enlarging opening 38 of sleeve 36. The enlarged opening 38 easily permits lower end 22 of ejector tube 10 to be inserted therein, or removed therefrom.

The improved socket 12 described above can be used advantageously with conventional dental saliva ejector tubes of the type already known. However, the dental saliva ejector tube 10 can be further improved by adding a generally circular rib 66 extending about the lower end 22 of saliva ejector tube 10. Rib 66 is of somewhat greater diameter than the outer wall of ejector tube 10. During insertion of lower end 22 of ejector tube 10 into opening 38 of sleeve 36, rib 66 is positioned below spreader members 40 and 42. When levers 44 and 56 are released, spreader members 40 and 42 engage rib 66 and lessen the likelihood that dental saliva ejector tube 10 can become inadvertently dislodged from socket 12. Nonetheless, rib 66 does not preclude rotation of the lower end 22 of ejector tube 10 within socket 12, as when the dentist desires to change the angle at which upper end 14 extends.

FIGS. 6–8 show a variation of the assembly already described above with respect to FIGS. 1–5, and features common to the embodiment shown in FIGS. 1–5 are identified by like reference numerals; in the embodiment shown in FIGS. 6–8, a single lever 58 is used to operate the device. Depression of lever 58 causes associated spreader member 40 to move apart from the central axis of central body 24 for enlarging the opening 38 of elastic sleeve 36. Second spreader member 42 of the embodiment of FIGS. 1–5 is replaced in the embodiment of FIGS. 6–8 with a rigid semicircular rib, or protuberance, 42' that is secured to the inner wall of elastic sleeve 36. Rib 42' is adapted to engage circular rib 66 on ejector tube 10, and along with spreader member 40, helps to prevent ejector tube 10 from being inadvertently dislodged. Rib 42' also serves to help stiffen the rightmost half (relative to FIGS. 7 and 8) of the upper portion of elastic sleeve 36; when spreader member 40 is moved away from the central axis of central body 24 due to depression of lever 58, as indicated by FIGS. 7 and 8, rib 42' provides enough rigidity to the rightmost half of elastic sleeve 36 as to allow opening 38 to widen, as indicated in FIGS. 7 and 8. Since only a single lever is used, metal bracket 46 can be formed as a single band, with opposed ears formed at the ends of such band, rather than two semicircular bands as was true for the dual lever Embodiment shown in FIGS. 1–5.

Referring now to the alternate embodiment of the vacuum line socket and dental saliva ejector tube assembly illustrated in FIGS. 9–12, the assembly includes a dental saliva ejector tube 110 identical to ejector tube 10 described above, as well as a vacuum line socket 112. Socket 112 includes a first (or lower) end 126 and a second (or upper) opposing end 128. A central passage 130 (see FIG. 12) extends between first end 126 and opposing second end 128 along a central axis 113 (see FIG. 12) for communicating a vacuum applied at first end 126 to second end 128. First end 126 includes a tapered port 132 for being coupled to a vacuum hose (not shown) which is in turn coupled to a source of a vacuum and waste depository. As indicated in FIGS. 9 and 12, tapered port 132 may include barbs 134 for retaining tapered port 132 onto the vacuum hose. Socket 112 is preferably made of plastic or hard rubber. While not shown in FIGS. 9 or 12, an optional control valve like that designated by reference numeral 35 in FIG. 3, may be incorporated within socket 112 to selectively close central passage 130 and block the vacuum source from reaching second end 128.

The second end 128 of socket 112 is adapted to receive the lower end of dental saliva ejector tube 110. In FIG. 9, the lower end of dental saliva ejector tube 110 is shown inserted within the second end 128 of vacuum line socket 112. Within FIGS. 10 and 12, the lower end of dental saliva ejector tube 110 is shown in dashed outline. Like ejector tube 10 of FIGS. 1-5, ejector tube 110 includes an enlarged diameter retaining rib 166 formed upon the lower end thereof.

The second or upper end 128 of socket 112 is relatively rigid, unlike the elastic sleeve described in reference to FIGS. 1–5. Upper end 128 of socket 112 is in the form of an oversized collar, having a diameter somewhat larger than the outer diameter of dental saliva ejector tubes received thereby. As shown best in FIG. 12, the central portion 133 of socket 112 has a reduced inner diameter along central passage 130 which is commensurate with the outer diameter of ejector tube 110. To enhance the seal formed between the lower end of ejector tube 110 and dentral passage 130, an elastomeric O-ring 131 can be disposed within central portion 133 surrounding central passage 130. Annular groove 135 is formed in the inner wall of central portion 133 to support O-ring 131. As shown in FIG. 12, the lower end of ejector tube 110 passes through O-ring 131 to form a relatively airtight seal between ejector tube 110 and socket 112.

It will be recalled that one of the objects of the present invention is to prevent ejector tube 110 from being inadvertently dislodged from socket 112. Toward such purpose, a pair of latch mechanisms 140 and 142 are provided generally proximate the second end 128 of socket 112 opposite one another. In the preferred embodiment shown in FIGS. 9–12, first and second latch mechanisms 140 and 142 extend through apertures formed in the wall of second end 128 in a manner which permits such latch mechanisms to slide back and forth in a radial direction. Preferably, the innermost ends of latch mechanisms 140 and 142 are arcuately shaped to match the outer diameter of ejector tube 110.

As shown in FIGS. 9 and 12, a metal bracket 146 encircles socket 112. Bracket 146 may be comprised of two metal strips, each including a semicircular middle region terminating in a pair of opposing flanges or ears 148 and 150 that extend in opposing directions away from socket 112. The two opposing strips of metal forming bracket 146 are secured to each other by hinge pins 152 and 154 which extend through the respective ears 148 and 150, respectively, of the two metal strips. Alternatively, bracket 146 can be eliminated, and the ears 148 and 150 can simply be molded extensions of socket 112.

As is further shown in FIGS. 9 and 12, first and second levers 144 and 156 are pivotally secured to socket 112 by hinge pins 152 and 154, respectively. The lower ends 158 and 160 of levers 144 and 156 are twisted through an angle of ninety degrees relative to the opposing upper ends of levers 44 and 56 to provide a control surface that can be easily depressed by a user's thumb and forefinger during use.

The upper end of first lever 144 is forked to provide two extensions 161 and 163. A pivot pin 165 extends through aligned apertures formed in extensions 161 and 163, and in the outermost end of latch mechanism 140. Thus, when the upper end of lever 144 moves away from central axis 113 of socket 112, latch mechanism 140 is pulled outwardly away from central axis 113. Likewise, the upper end of second lever 156 is preferably forked to provide two extensions 167 and 169. A pivot pin 171 extends through aligned apertures formed in extensions 167 and 169, and in the outermost end of latch mechanism 142. Thus, when the upper end of second lever 156 moves away from central axis 113 of socket 112, latch mechanism 142 is pulled outwardly away from central axis 113. While the preferred embodiment illustrated in FIGS. 9–12 includes two levers and two latch mechanisms, those skilled in the art will appreciate that such assembly can be modified to operate in single-lever fashion; in this instance, one such lever (for example, second lever 156) is omitted, and one of the latch mechanisms (for example, second latch mechanism 142 is simply fixed, as by molding a semicircular ridge or protuberance upon the inner wall of second end 128 of socket 112 opposite latch mechanism 140.

As shown in FIGS. 9 and 12, an elastic band 173 encircles first and second levers 144 and 156 near their upper ends, i.e., above pivot pins 152 and 154. This elastic band acts as a means for biasing the upper ends of levers 144 and 156 toward the central axis 113; hence, elastic band 173 biases the innermost arcuate ends of latch mechanisms 140 and 142 toward the central axis 113, and toward one another.

As shown in FIG. 10, the arcuate innermost ends of latch mechanisms 140 and 142 are adapted to engage the outer walls of ejector tube 110, and to interfere with the enlarged diameter retaining rib 166 formed upon the lower end thereof. When a user desires to either insert ejector tube 110 into socket 112, or to remove ejector tube 110 from socket 112, the user squeezes the lower ends of levers 144 and 156, in the manner designated by the large arrows in FIG. 12, to move the upper ends of levers 144 and 156 apart from each other against the biasing force applied by elastic band 173. This action in turn causes first and second latch mechanisms 140 and 142 to move away from central axis 113 of socket 112, apart from each other, away from the lower end of ejector tube 110, and away from retaining rib 166, thereby allowing ejector tube 110 to be inserted within, or released from, second end 128 of vacuum line socket 112.

Those skilled in the art will now appreciate that an improved dental saliva ejector tube assembly has been described which simplifies the insertion of the dental saliva ejector tube into the socket, and which allows the dental saliva ejector tube to be easily removed therefrom when a dentist has finished working upon a dental patient. The disclosed dental saliva ejector tube assembly can be used with conventional dental saliva ejector tubes and does not significantly increase the cost of current vacuum line sockets. Moreover, the optional addition of the rib to the lower end of the dental saliva ejector tube makes it less likely to inadvertently dislodge the dental saliva ejector tube from the vacuum line socket, yet still allows the dental saliva ejector tube to be rotated following insertion to change the angle at which the bent upper end of the dental saliva ejector tube extends relative to the vacuum line socket. While the present invention has been described with respect to preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

I claim:

1. A socket for removably receiving an end of a dental saliva ejector tube, said socket comprising in combination:
   a. a central body extending along a central axis and having first and second opposing ends and a central passage extending therebetween, the first end including a port for being coupled to a source of a vacuum;
   b. an elastic sleeve secured to and extending about the second end of said central body, said sleeve having an opening for receiving the end of the dental saliva ejector tube;
   c. a spreader member disposed proximate the opening of said sleeve for enlarging the opening of said sleeve; and
   d. a lever pivotally secured to said central body and coupled with said spreader member, said lever being adapted to be actuated by a user for causing said spreader member to move apart from the central axis of said central body for enlarging the opening of said sleeve.

2. The socket recited by claim 1 wherein the opening of said sleeve is circular, and wherein said spreader member is arcuate.

3. The socket recited by claim 1 wherein said spreader member is disposed inside the opening of said sleeve.

4. The socket recited by claim 1 including a bracket secured about said central body, said lever being pivotally supported by said bracket.

5. The socket recited by claim 1 wherein the port of said central body is barbed for ecurely receiving a vacuum hose.

6. The socket recited by claim 1 wherein said central body includes a valve for selectively closing the central passage extending therethrough.

7. A dental saliva ejector tube assembly comprising in combination:
   a. a dental saliva ejector tube having an upper end for extending into a patient's mouth and having a lower end for coupling to a vacuum; and b. a socket including:
      i. a central body extending along a central axis and having first and second opposing ends and a central passage extending therebetween, the first end including a port for being coupled to a source of a vacuum;
      ii. an elastic sleeve secured to and extending about the second end of said central body, said sleeve having an opening for receiving the lower end of said dental saliva ejector tube;
      iii. a spreader member disposed proximate the opening of said sleeve for enlarging the opening of said sleeve when said spreader member is moved away from the central axis of the central body; and
      iv. a lever pivotally secured to said central body and coupled with said spreader member, said lever being adapted to be actuated by a user for causing said spreader member to move apart from the central axis for enlarging the opening of said sleeve in order to engage or disengage the lower end of said dental saliva ejector tube.

8. The dental saliva ejector tube assembly recited by claim 7 wherein the lower end of said saliva ejector tube is circular, wherein the opening of said sleeve is circular, and wherein said spreader member is arcuate.

9. The dental saliva ejector tube assembly recited by claim 7 wherein the lower end of said saliva ejector tube includes a generally circular rib extending thereabout to lessen the likelihood that said dental saliva ejector tube can become inadvertently dislodged from said socket.

10. The dental saliva ejector tube assembly recited by claim 7 wherein said spreader member is disposed inside the opening of said sleeve.

11. The dental saliva ejector tube assembly recited by claim 7 including a bracket secured about said central body, said lever being pivotally supported by said bracket.

12. The dental saliva ejector tube assembly recited by claim 7 wherein the port of said central body is barbed for securely receiving a vacuum hose.

13. The dental saliva ejector tube assembly recited by claim 7 wherein said central body includes a valve for selectively closing the central passage extending therethrough.

14. A vacuum line socket and dental saliva ejector tube assembly, comprising in combination:
   a. a dental saliva ejector tube having a first end for being inserted into a patient's mouth and having a second end, said second end having an enlarged diameter retaining rib formed thereupon;
   b. a vacuum line socket having first and second opposing ends and a central passage extending therebetween, the first end including a port for being coupled to a source of a vacuum, and the second end forming a socket for receiving the second end of the dental saliva ejector tube, the central passage extending along a central axis;
   a lever pivotally secured to said vacuum line socket, said lever including a first end adapted to be actuated by a user and having an opposing second end;
   d. a latch mechanism associated with the second end of said lever and disposed generally proximate the second end of said vacuum line socket, said latch mechanism being adapted to engage the enlarged diameter retaining rib formed upon said dental saliva ejector tube when the first end of said lever is not actuated by a user, and wherein actuation of the first end of said lever causes the second end of said lever and said latch mechanism associated therewith to move away from the central axis, away from the second end of said dental saliva ejector tube, and away from the enlarged diameter retaining rib formed thereupon, for allowing said dental saliva ejector tube to be inserted within, or released from, the second end of said vacuum line socket; and
   e. a biasing means for biasing said latch mechanism toward the central axis of the central passage of said vacuum line socket.

15. vacuum line socket and dental saliva ejector tube assembly recited by claim 14 including a bracket secured about said vacuum line socket, said lever being pivotally supported by said bracket.

16. The vacuum line socket and dental saliva ejector tube assembly recited by claim 14 wherein the port provided at the first end of said vacuum line socket is barbed for securely receiving a vacuum hose.

17. The vacuum line socket and dental saliva ejector tube assembly recited by claim 14 wherein said vacuum line socket includes a valve for selectively closing the central passage extending therethrough.

18. The vacuum line socket and dental saliva ejector tube assembly recited by claim 14 wherein said biasing means also biases the second end of said lever toward the central axis of said vacuum line socket.

19. The vacuum line socket and dental saliva ejector tube assembly recited by claim 14 wherein said biasing means is an elastic member.

20. The vacuum line socket and dental saliva ejector tube assembly recited by claim 14 wherein the central passage of said vacuum line socket includes a flexible O-ring generally proximate the second end of said vacuum line socket to receive, and form a seal about, the second end of said dental saliva ejector tube.

21. The vacuum line socket and dental saliva ejector tube assembly recited by claim 14 including a second lever pivotally secured to said vacuum line socket opposite said first lever, said second lever including a first end adapted to be actuated by a user and having an opposing second end, further including a second latch mechanism associated with the second end of said second lever and disposed generally proximate the second end of said vacuum line socket opposite said first latch mechanism, said second latch mechanism being adapted to engage the enlarged diameter retaining rib formed upon said dental saliva ejector tube when the first end of said second lever is not actuated by a user, and wherein actuation of the first end of said second lever causes the second end of said second lever and said second latch mechanism associated therewith to move away from the central axis, away from the second end of said dental saliva ejector tube, and away from the enlarged diameter retaining rib formed thereupon, for allowing said dental saliva ejector tube to be inserted within, or released from, the second end of said vacuum line socket, said biasing means biasing said second latch mechanism toward the central axis of the central passage of said vacuum line socket.

22. A vacuum line socket and dental saliva ejector tube assembly, comprising in combination:
  a. a dental saliva ejector tube having a first end for being inserted into a patient's mouth and having a second end, said second end having an enlarged diameter retaining rib formed thereupon;
  b. a vacuum line socket having first and second opposing ends and a central passage extending therebetween, the first end including a port for being coupled to a source of a vacuum, and the second end forming a socket for receiving the second end of the dental saliva ejector tube, the central passage extending along a central axis;
  c. first and second latch mechanisms disposed generally proximate the second end of said vacuum line socket opposite one another and adapted to engage the enlarged diameter retaining rib formed upon the second end of said dental saliva ejector tube;
  d. biasing means for biasing said first and second latch mechanisms toward the central axis of the central passage of said vacuum line socket and toward one another;
  e. first and second levers pivotally secured to said vacuum line socket, said first lever being associated with said first latch mechanism, and said second lever being associated with said second latch mechanism, said first and second levers being adapted to be actuated by a user for causing said first and second latch mechanisms to move away from the central axis of the central passage of said vacuum line socket, and apart from each other, away from the second end of said dental saliva ejector tube, and away from the enlarged diameter retaining rib formed thereupon, for allowing said dental saliva ejector tube to be inserted within, or released from, the second end of said vacuum line socket.

23. The vacuum line socket and dental saliva ejector tube assembly recited by claim 22 including a bracket secured about said vacuum line socket, said first and second levers being pivotally supported by said bracket.

24. The vacuum line socket and dental saliva ejector tube assembly recited by claim 22 wherein the port provided at the first end of said vacuum line socket is barbed for securely receiving a vacuum hose.

25. The vacuum line socket and dental saliva ejector tube assembly recited by claim 22 wherein said vacuum line socket includes a valve for selectively closing the central passage extending therethrough.

26. The vacuum line socket and dental saliva ejector tube assembly recited by claim 22 wherein said biasing means includes an elastic member.

27. The vacuum line socket and dental saliva ejector tube assembly recited by claim 22 wherein said biasing means engages the second ends of said first and second levers for biasing the second ends of said first and second levers toward the central axis of said vacuum line socket.

28. The vacuum line socket and dental saliva ejector tube assembly recited by claim 22 wherein the central passage of said vacuum line socket includes a flexible O-ring generally proximate the second end of said vacuum line socket to receive, and form a seal about, the second end of said dental saliva ejector tube.

* * * * *